(12) United States Patent
Linné

(10) Patent No.: US 9,918,644 B2
(45) Date of Patent: Mar. 20, 2018

(54) METHOD FOR EXAMINING THE SURFACE TEMPERATURE OF A BODY PART

(75) Inventor: Anders Linné, Luleå (SE)

(73) Assignee: Performance in Cold AB, Luleåa (SE)

( * ) Notice: Subject to any disclaimer, the term of this patent is extended or adjusted under 35 U.S.C. 154(b) by 990 days.

(21) Appl. No.: 13/879,016

(22) PCT Filed: Oct. 14, 2010

(86) PCT No.: PCT/SE2010/051111
§ 371 (c)(1),
(2), (4) Date: Jun. 24, 2013

(87) PCT Pub. No.: WO2012/050495
PCT Pub. Date: Apr. 19, 2012

(65) Prior Publication Data
US 2014/0148705 A1    May 29, 2014

(51) Int. Cl.
*A61B 6/00* (2006.01)
*A61B 5/01* (2006.01)
(Continued)

(52) U.S. Cl.
CPC .......... *A61B 5/015* (2013.01); *A61B 5/0075* (2013.01); *A61B 5/0077* (2013.01); *A61B 5/01* (2013.01); *A61B 5/0261* (2013.01); *A61B 5/70* (2013.01)

(58) Field of Classification Search
None
See application file for complete search history.

(56) References Cited

U.S. PATENT DOCUMENTS

| 4,428,382 A * | 1/1984 | Walsall | A61B 5/015 600/549 |
| 5,810,010 A * | 9/1998 | Anbar | A61B 5/015 600/407 |

(Continued)

FOREIGN PATENT DOCUMENTS

| CN | 101617938 A | 1/2010 |
| EP | 0885587 A1 | 12/1998 |

(Continued)

OTHER PUBLICATIONS

Murray et al., "Noninvasive Imaging Techniques in the Assessment of Scleroderma Spectrum Disorders." Arthritis & Rheumatism, vol. 61, No. 8, Aug. 15, 2009, pp. 1103-1111.*

(Continued)

*Primary Examiner* — James Kish
(74) *Attorney, Agent, or Firm* — Morrison & Foerster LLP

(57) ABSTRACT

The blood circulation in a body part may be affected by various factors such as burns, vibration, smoking, drugs, physical activity, adhesion, medical treatment, acupuncture, light therapy, ambient temperature, injuries such as sprains and broken bones, diseases and various foodstuffs. The invention relates to a method for examining the surface temperature of a body part due to such factors. The method according to the invention comprises an initial period in which the body part is positioned in a background screen and photographed with a thermographic camera, an exposure period in which body part is exposed to a refrigerant for a predetermined exposure time, a recovery period in which body part is repositioned in the background screen and photographed or filmed with a thermographic camera. The invention also relates a system for examination of the surface temperature of a body part according to the method.

(Continued)

The device includes a thermographic camera connected to a computer and a background screen that makes it possible to find and scan body parts. The blood circulation in a body part may be affected by various factors such as burns, vibration, smoking, drugs, physical activity, adhesion, medical treatment, acupuncture, light therapy, ambient temperature, injuries such as sprains and broken bones, diseases and various foodstuffs. The invention relates to a method for examining the surface temperature of a body part due to such factors. The method according to the invention comprises an initial period in which the body part is positioned in a background screen and photographed with a thermographic camera, an exposure period in which body part is exposed to a refrigerant for a predetermined exposure time, a recovery period in which body part is repositioned in the background screen and photographed or filmed with a thermographic camera. The invention also relates a system for examination of the surface temperature of a body part according to the method. The device includes a thermographic camera connected to a computer and a background screen that makes it possible to find and scan body parts.

10 Claims, 7 Drawing Sheets

(51) Int. Cl.
*A61B 5/026* (2006.01)
*A61B 5/00* (2006.01)

(56) References Cited

U.S. PATENT DOCUMENTS

| | | | |
|---|---|---|---|
| 7,214,195 B2 * | 5/2007 | Mitra | A61B 5/015 600/473 |
| 2010/0030083 A1 | 2/2010 | Sanders et al. | |
| 2010/0041998 A1 | 2/2010 | Postel | |

FOREIGN PATENT DOCUMENTS

| | | | |
|---|---|---|---|
| EP | 1212977 A1 | 6/2002 | |
| GB | 2203835 A | 10/1988 | |
| GB | 2311368 A | 9/1997 | |
| JP | 2004-16734 A | 1/2004 | |
| JP | 2006-247126 A | 9/2006 | |
| WO | 2001/12067 A1 | 2/2001 | |
| WO | WO 2011/000918 | * 1/2011 | A61B 5/00 |

OTHER PUBLICATIONS

Schaefer et al., "Automated Overlay of Infrared and Visual Medical Images." IGI Global, 2008, pp. 166-175.*
Hejazi et al., "Simultaneous Acquisition of Thermal and Visible Images in a Scanning Infrared Camera." SPIE vol. 2020 Infrared Technology XIX, 1993, pp. 510-516.*
International Preliminary Report on Patentability received for PCT Patent Application No. PCT/SE2010/051111, dated Apr. 25, 2013, 6 pages.
International Written Opinion received for PCT Patent Application No. PCT/SE2010/051111, dated Jun. 22, 2011, 4 pages.
International Search Report received for PCT Patent Application No. PCT/SE2010/051111 dated Jun. 22, 2011, 5 pages.

* cited by examiner

METHOD FOR EXAMINING THE SURFACE TEMPERATURE OF A BODY PART

CROSS REFERENCE TO RELATED APPLICATION

This application is a U.S. National Phase patent application of PCT/SE2010/051111, filed Oct. 14, 2010, which is hereby incorporated by reference in the present disclosure in its entirety.

FIELD OF INVENTION

The present invention relates to a method for examining the surface temperature of a body part which comprises a body surface divided into multiple measuring zones. The invention also relates to a device for examining the surface temperature of a body part and a computer program for carrying out the method and a memory medium.

BACKGROUND

Individual performance is particularly influenced by exterior circumstances such as cold climate. Parameters such as low surrounding temperature or vibrations impair the blood circulation to the outer parts of the body, making body parts colder.

Lack of or poor circulation can have serious consequences such as permanently damaged tissue and sensory loss. Poor circulation also affects the mental ability of an individual. In very severe cases non-existent blood circulation can lead to amputation or similar interventions.

SUMMARY OF INVENTION

One object of the invention is to provide a simple, standardized, fast, clear, reliable, precise and repeatable method for examination of the surface temperature of a body part. This aim is achieved by a method having method steps defined by the disclosure below.

Another object of the invention is to provide a portable, easy to use system for examination of the surface temperature of a body part. This object is achieved by a system comprising the features defined by the disclosure below.

Further advantageous embodiments of the invention are defined below.

Infrared radiation is emitted by any object that has a temperature above −273° C. and can be detected by a thermographic camera. A thermographic camera can thus detect the infrared radiation emitted from a body part and render the surface temperature of the photographed or filmed part of the body. The temperature of the surface of the object is represented on the resulting image or film by different colors, and depending on the camera's sensitivity, good resolution of the temperature variations can be obtained.

The surface temperature of a body part is considered to be an indication of how well the blood circulation in the body part functions.

One advantage of the invention is that a person can be helped to improve his/her performance at work or sports in cold climate.

The results of the examination shows how the examined body surface is influenced by being cooled down, and to which extent different areas of the body surface are affected. The results can be used for selecting and adaptation of different body protections and helping facilities such as gloves, shoes, tools and other body protecting means.

Another advantage is that the results of the examination can be used for showing how a cold surrounding climate influences a body part and the blood circulation of the body part in a pedagogical manner. Thereby are persons also made aware of the risks and limitations related to work or other types of performance in cold climate.

The method according to the invention is unique since the surface temperature of the entire body surface of a body part and not just individual points are measured. For example, the surface temperature of the entire face is measured, a whole palm or the entire foot sole. Both the left and right body part (hand, foot, cheek, ear) can be examined simultaneously, thus an automatic reference between the right and left body part is received and by comparing the surface temperatures on corresponding surfaces deviations can be identified.

The method can be used for examining if the blood circulation is affected by a number of different parameters. Internal factors may consist of a food, such as food or drink, a drug or the like.

External parameters may include cold, heat, a vibrating device, acupuncture, light therapy or the like. In the example of the method below the body part is exposed to a refrigerant. The method has proven to be particularly good for detecting frost bites and vibration damages on the examined body part with this type of provocation. It is known that frost bites and vibration damages decreases the blood circulation.

In order to simplify and increase safety in the analysis, background information on previous problems like injuries, smoking habits, loss of sensation and other personal type of information is collected with a questionnaire in advance of the examination. Answers from the questionnaire can be directly related to results from a measurement zone, thus underlying causes of discrepancies can be identified.

BRIEF DESCRIPTION OF DRAWINGS

Further objects and features of the present invention will appear from the following detailed description of some aspects of the invention, wherein some aspects will be described in more detail with reference to the accompanying drawings, in which.

The following description and the patent claims define several embodiments of the invention. All embodiments can be combined in a variety of ways while still achieving the advantages and benefits of the invention.

DETAILED DESCRIPTION

Figure 1:
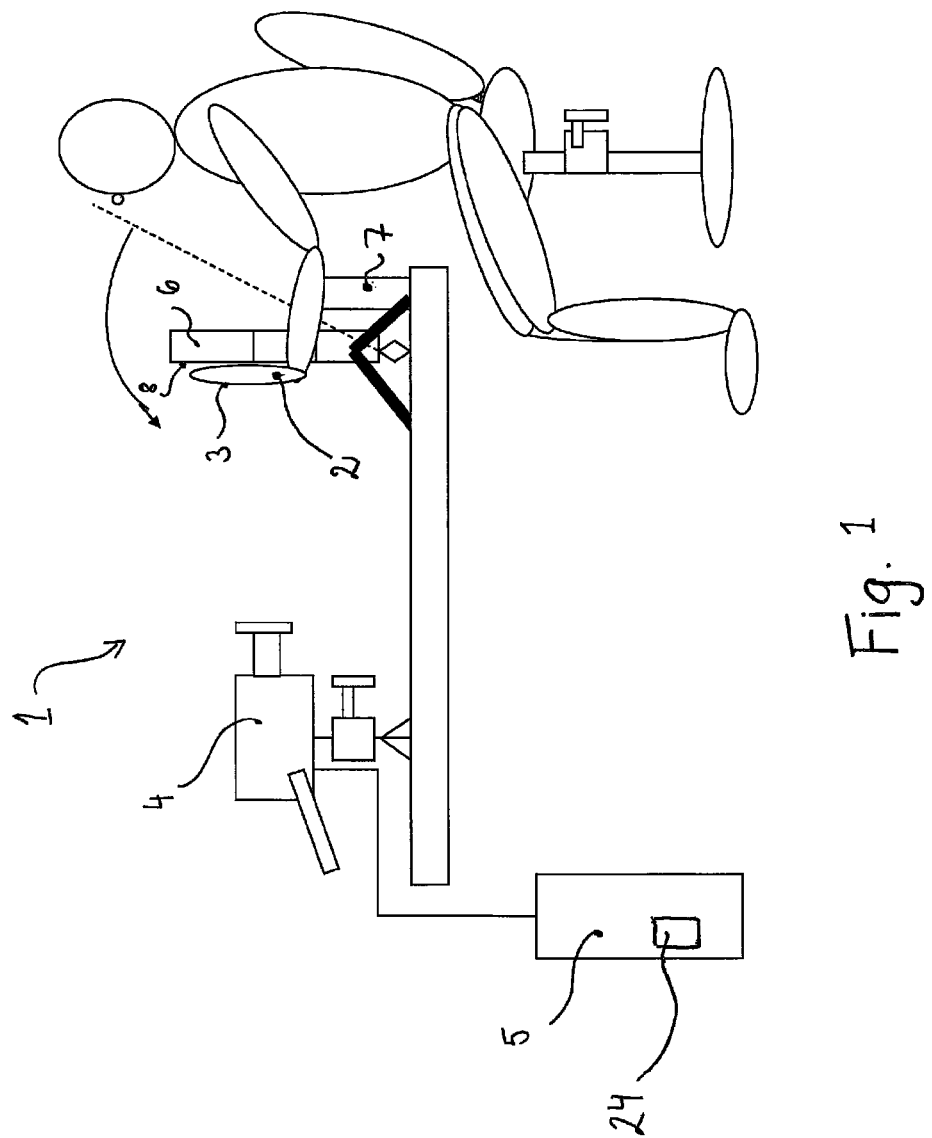
FIG. 1 shows a schematic view of a system according to the invention.

FIG. 1 shows a system 1 for examination of the surface temperature of a body part 2 which comprises a body surface 3 divided into a number of measuring zones according to the invention. The system is provided with means for carrying out the method according to the invention.

The system 1 comprises a thermographic camera 4 for photography and filming, a computer 5 that is connected to the thermographic camera, a background screen 6 for the body part and support pads 7 for the body part.

The background screen 6 comprises a flat panel 8 of background material which is intended to prevent body heat from other parts of the body of the person to influence the examination and the resulting measurements.

Figure 2:
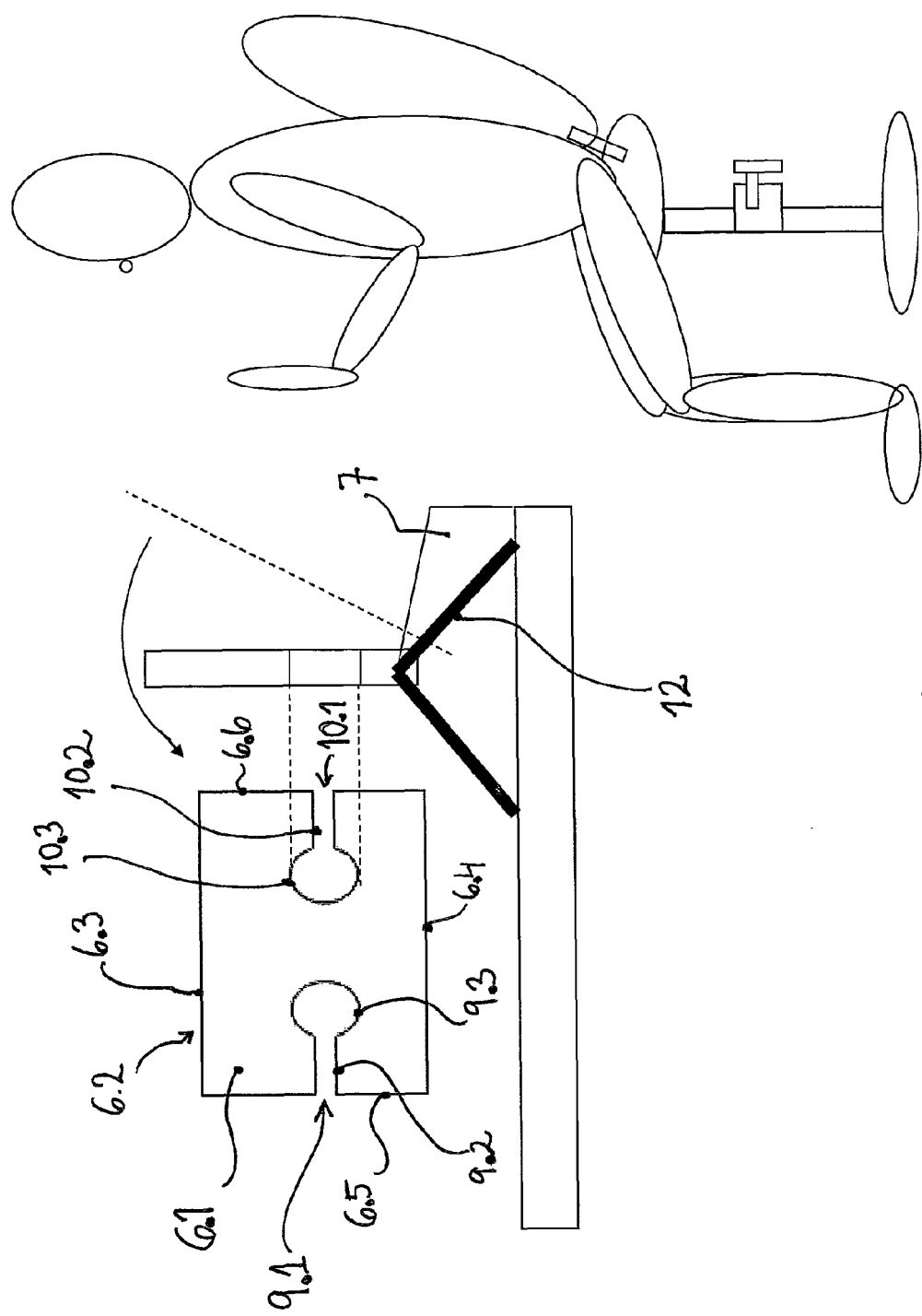
FIG. 2 shows a side view and a front view of the background screen shown in FIG. 1.
Figure 3:
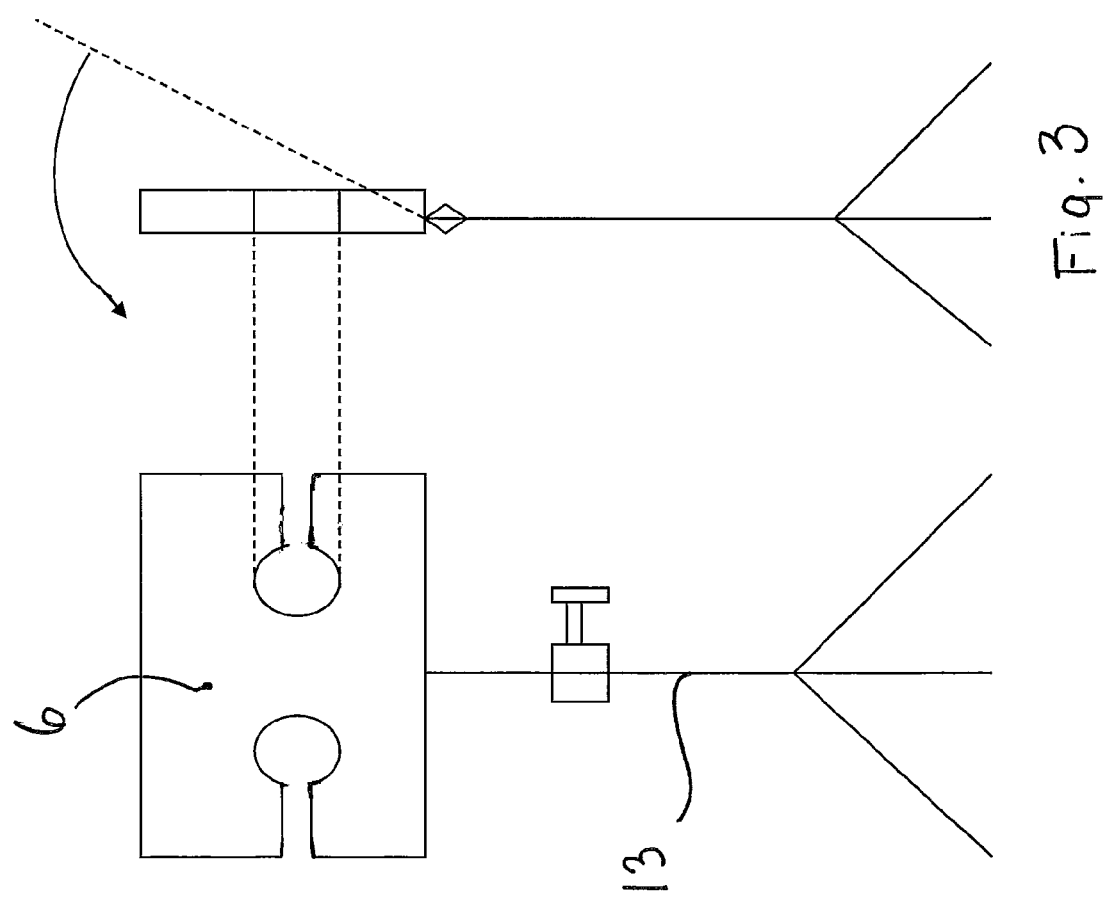
FIG. 3 shows a side view and a front view of a background screen.

The background screen 6 comprises a front side 6.1 and a back side 6.2, an upper edge 6.3, a lower edge 6.4, a first side edge 6.5 and a second side edge 6.6, see FIG. 2.

The background screen 6 has at least one opening 9.1; 10.1, or through hole, which has an entry channel 9.2;10.2 stretching from at least one side edge of the background screen to a placement space 9.3;10.3. The body part 2 is positioned next to the background screen by passing the body part through the entry channel 9.2;10. and positioning the body part within the placement space 9.3;10.3. The body part 2 which is going to be examined is thereby located on the front side 6.1 of the background screen, and other body parts of the person are located on the rear side 6.2 of the screen.

The background screen is provided a supporting legs 12 that can be placed on a table or a supporting stand 13 that can be placed on the floor.

The supporting legs 12 and the supporting stand 13 are provided with means for adjusting the height of the screen. The background screen can be tilted angularly to the front and rear to achieve an optimized and comfortable position for the person.

The size of the screen is adapted such that the body part is positioned well within the area limited by the edges of the screen.

The openings 9.1;10.1 and placement spaces 10.1;10.2 are arranged so that body part is exposed on the front side 6.1 of the background screen and within the area limited by the edges of the screen.

The screen comprises on or more adjacently positioned panels of radiant heat insulating material or a plastic sheet or another material with low thermal conductivity so that the background screen temperature does not influence the result of the examination.

Figure 4:
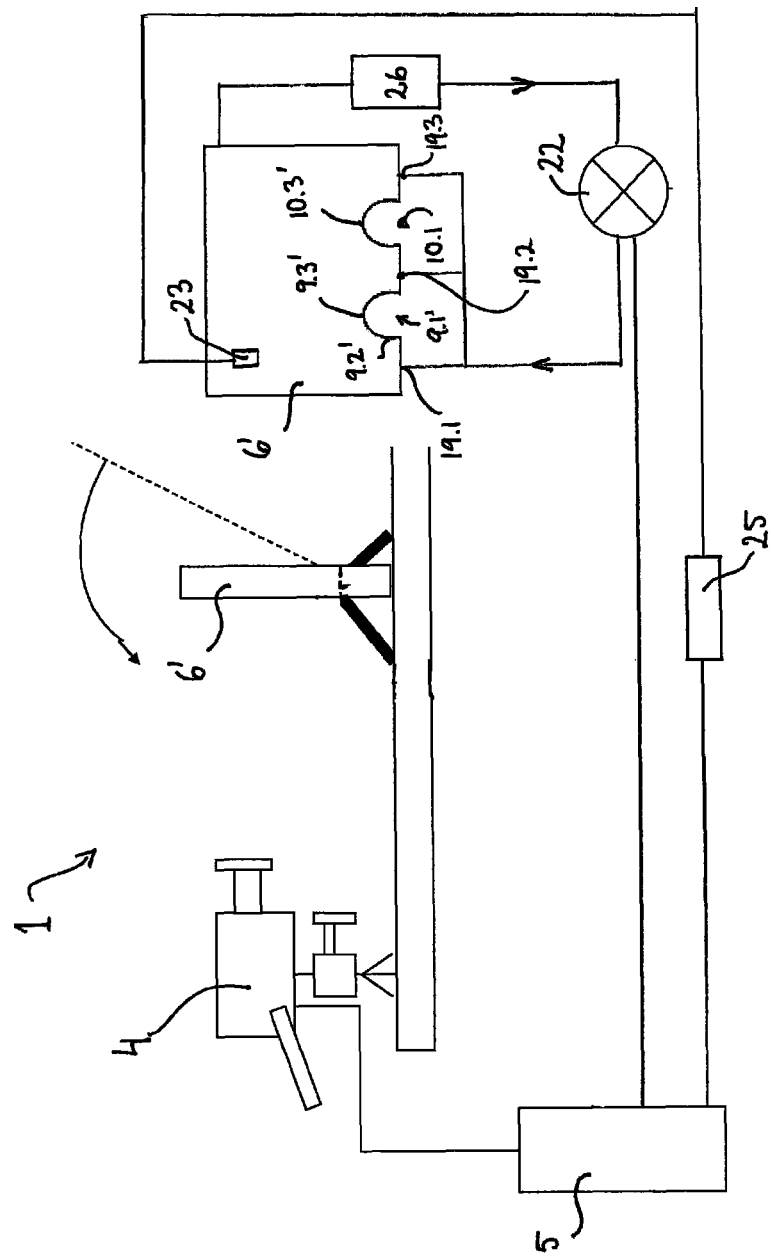
FIG. 4 shows a schematic view of a system according to the invention and a side view and a front view of a background screen.

FIG. 4 shows another background screen 6' that has a first opening 9.1' and a second opening 10.1'. The first and the second opening each have a channel 9.2':10.2' stretching from the lower edge of the background screen to the placement spaces 9.3';10.3'.

Figure 5:
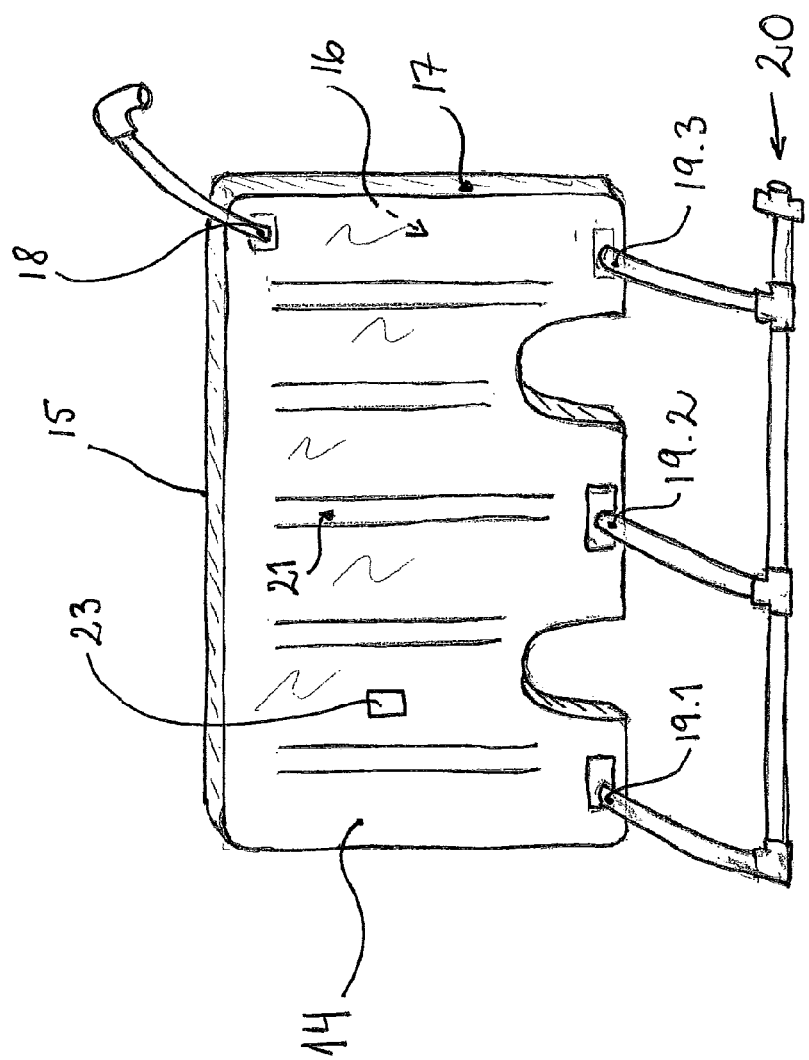
FIG. 5 shows a detailed view of another embodiment of the background screen shown in FIG. 4.

FIG. 5 shows a detailed view of another embodiment of the background screen shown in FIG. 4.

The background screen 6' is provided with means for cooling or heating the screen. The temperature of the screen can thereby be kept lower or higher than temperature of the body surface of the body part.

This is has the advantage that the temperature of the background screen is controlled. It is important to avoid sources of errors in the examination. By controlling the temperature of the screen the influence of other heat sources, like other body parts, on the examination and temperature measurements are lowered. This improves the results of the examination.

Preferably the temperature of the background screen is regulated so that the background is at least 2 degrees Celsius warmer or colder (+/−2° C.) of the body surface throughout the whole examination process to allow and secure the scanning of a body parts measuring zone.

The background screen 6' comprises a front panel 14 and a rear panel 15. The material of the panels is for example a transparent plastic panel or similar material. The panels 14, 15 are arranged in parallel and with a distant between them such that a gap 16 is formed between the panels. The front and the rear panel are joined to each other along the outer edges of the panels, such that the gap forms a closed and sealed inner space 17. The background screen 6' has at least at least one inlet 19.1;19.2;19.3 to the inner space and at least one outlet 18 from the inner space to allow a cooling or heating medium, for example heated water or cold water, to flow through the space from the inlet to the outlet.

The front and the rear panel are also joined by distancing supports, ribs, 21 which are located within the inner space 17 to keep the front panel and the rear panel securely in place.

A pump 22 is connected by pipes to the inlet and to the outlet of the background screen. The pump circulates the medium through the inner space of the background screen. The medium can be provided by a closed container 26 connected to the pump. The container has means for providing that the medium is kept at the desired temperature, such as heating means or cooling means (not shown in figures). The screen is provided with thermocouples 23 to measure the temperature of the screen. The thermocouples are connected to a controlling unit 25 and the computer 5.

Another embodiment of the background screen comprises an electrically heated panel of a foil like material for heating the screen (not shown in the figures).

Another embodiment of the background screen comprises an cooling panel of a foil like material provided with heat exchanging means for cooling the screen (not shown in the figures).

The system comprises support pads 7 for the body parts which is/are located on the rear side of the screen.

The support pads 7 can be designed as a bowl-shaped or cup-shaped supporting surface that a heel can rest in. When hands are examined, the palms of the hands are facing forwards, towards the thermographic camera. When a foot or a couple of feet are examined, the heels are resting in the cup-shaped support, positioning the soles of the feet forwards and towards the camera.

Hands and feet are placed in a high position (raised). This means that the hands are held at chest height. Preferably the person sits on a height adjustable chair. When examining the feet, the person lays flat on his/her back with the legs aligned and straight and the feet are held such that the foot soles are facing the camera.

The use of background screen 6 with the support pads for a body part ensures that the same position for the body part is found and maintained throughout the examining period, both during the initial period and during the recovery period when digital photographing or filming with thermo graphic camera is carried out.

The system comprises a thermographic camera 4 for digital photography and filming of traditional and thermograhic images and a computer 5 that is connected to the thermographic camera. The thermographic camera is used for digital photography and digital filming of traditional images and thermographic images.

By photographing of traditional images is meant conventional monochrome or color photography. The thermographic camera 4 is directly connected to the computer which has a CPU, a monitor, a webcam and a memory device 24 for storing the information data collected during the examination procedure. A computer program is loaded into an internal memory of the computer. The computer program comprises the code parts of the computer program product for carrying out the method when it is executed on the computer. It is advantageous to provide the computer with means and programs for image processing. The computer and the webcam can be connected to Internet to allow other people which are not present, to study the examination procedure.

The computer program have means for locating and programming the scanning position for the body part to ensure that the same scanning position for the body part is located and scanned over the entire examination period, both at the initial period and during the recovery period when digital photographing and filming with thermographic camera are carried out. For example, means for image processing and image processing programs can be used for this.

All information data reported and/or executed by the computer and the computer program are stored in a database after the examination procedure is completed.

A traditional image and/or a thermographic image are digitally photographed by the thermographic camera and the image/s are transferred to the computer and the monitor. The images are then monitored, controlled and processed by the computer. The thermographic image reflects the variations of the surface temperature on the examined body part. The thermographic image shows the surface temperature in a very large number of points on the examined body part.

The thermographic image has a very high resolution, for example, one camera has a resolution equivalent to 640×480 pixels. One pixel shows the surface temperature on one picture point, scanning spot, on the surface of the body part. The surface temperature in a very large number of points on the body surface are thus individually examined and measured at the same time.

The computer program comprises 1.2 . . . n predefined body surface measuring zones hereafter referred to as M(1–n) for one or two hands, and one or two feet, one or two arms, one or two legs, a full face or part of a face, a neck, a back of neck, one or two ears, one or two cheeks.

The traditional image and/or the thermographic image of the scanned surface of the body part is/are displayed on the monitor, the computer screen.

Figure 6:
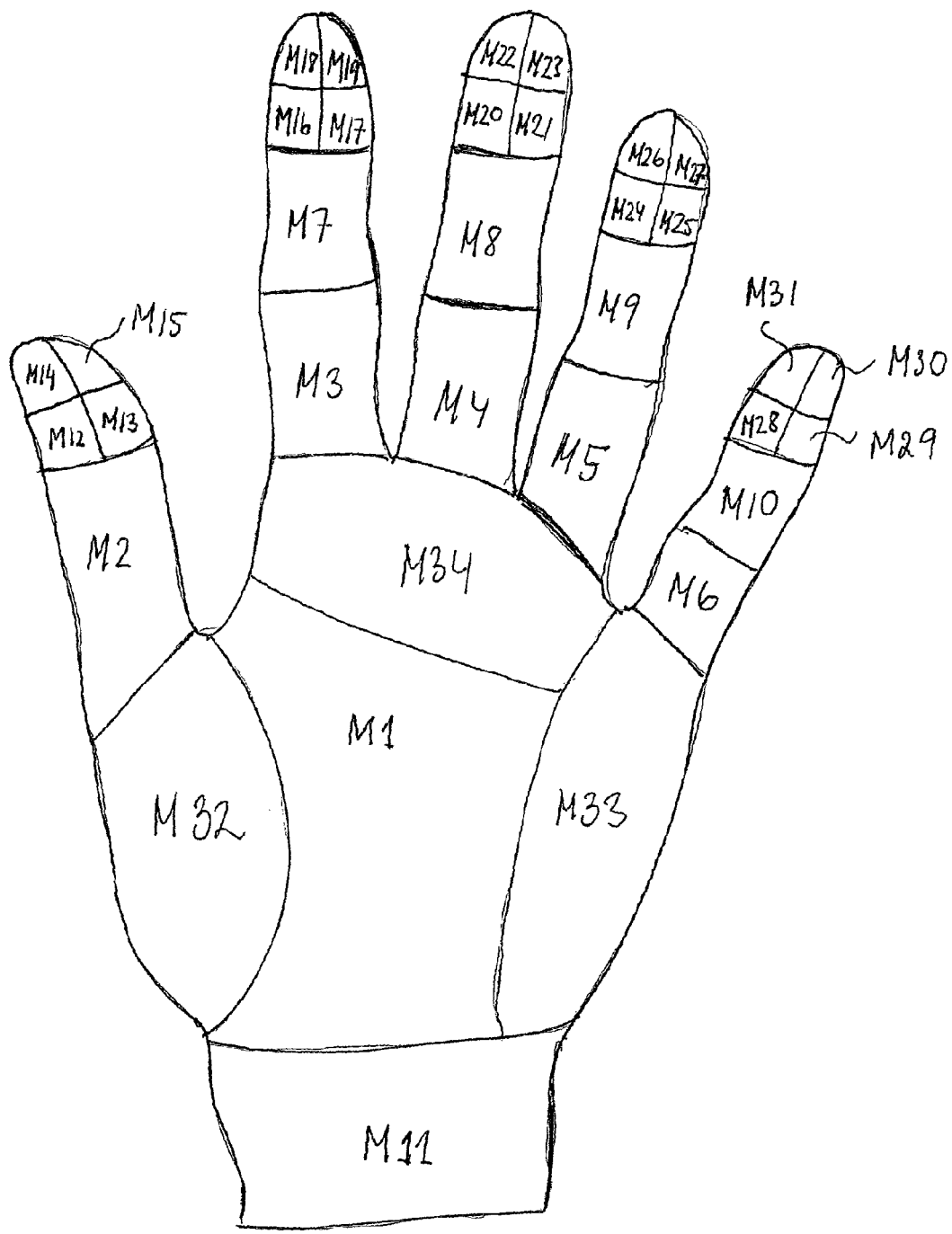
FIG. 6 shows an example of a body surface.

The thermographic camera 4 comprises at least one predefined measuring zone M(1–n). The traditional image and/or the thermographic image of the surface of the body part is/are divided into the corresponding measuring zones M (1–n). For example, the image of each hand is divided into upto 34 zones, M (1, 2 . . . 34), namely fingertips (distal phalanges), upper intermediate fingers (intermediate phalanges), lower intermediate fingers (proximal phalanges), palms (metacarpals) and wrist (carpals). The fingertips are particularly vulnerable, thus the image of each fingertip are further divided into four measuring zones. FIG. 6 shows a right hand with measuring zones M(1-34).

The computer program processes and saves the body surface temperature values measured by the thermographic camera and calculates the average temperatures and temperature anomalies from all measuring zones M (1–n) in each batch, also called scanning, which will be further described below.

The computer 5 also has a reporting program that illustrates the recovery process during and after the examination and measurement procedure.

The system is also provided with a database for storing the images, all measuring data and information such as room temperature, medium temperature, body temperature, heart rate and blood pressure and all the measured and calculated values for surface temperatures and instants of time, exposure periods, duration of recovering period etc.

At the setup of the system for examining a body part, the distance between the body part/s which are to be examined and the thermographic camera and the angle of the thermographic camera are adjusted. The body part/s are positioned in front of the background screen and within the area limited by the outer edges of the background screen.

After the adjusting operation, the thermographic camera scans the surface of the body part and transfers the information to the computer and the computer program. Thereafter is the body part photographed and/or filmed by the camera.

Based on the first image, the measuring zones M (1–n) and their coordinates can be mutually positioned and adjusted manually by clicking and dragging with a mouse cursor on the computer screen.

Before the examination, the test person should be at rest at room temperature with a minimum of plus 20° C., at least 30 minutes. The individual must not smoke or snuff tobacco 4 hours before measurement since such activities lowers the body temperature 4 degrees on the fingertips and toes. During the resting period the test person should be fasting and not drink hot drinks, or sit with their hands together. Body parts that are going to be tested must be completely at rest. It is essential that the person does not put the body parts that ar going to be examined on any cold or hot surfaces, to avoid error sources.

Measurement and documentation is carried out throughout the whole examination period which comprises an initial period from the time the first image is photographed, an exposure period and a recovery period that ends when a final image is photographed after recovery has occurred. In the description and the example of the method below temperature is indicated by T and time is indicated by t.

The method for examination of the surface temperature of a body part which comprises a body surface divided into a number of measuring zones comprises positioning of the body part in a system for examining a body part, wherein the system has a thermographic camera, and digitally photographing essentially the entire body surface that is directed towards the thermographic camera both as a traditional image and as a thermographic image during an initial period, exposing the body part to a refrigerant during a predetermined exposure time during an exposure period, repositioning the body part in the system for examining the body part, and digitally photographing the body surface as a traditional image, and filming the body surface as a thermographic film or repetitively digitally photographing the body surface as thermographic images during a recovery period.

The body surface temperature in a large number of picture points are thereby measured with the thermographic camera and indicated on the thermographic image.

The following is an embodiment of the method according to the invention:

The Initial Period

The body temperature is measured with an ear thermometer, heart rate and blood pressure measured with blood pressure measuring device, the surrounding room temperature is measured and recorded, the refrigerant temperature and the temperature of the background screen 6' are measured and recorded with the thermographic camera 4 and the temperature of the background screen is set and can be regulated to be maintained within +/−2 degrees Celcius higher or lower temperature than the body parts that are examined throughout the whole examination period. The body parts which are going to be examined are positioned against the background screen 2 for the examination and measuring by photographing. The camera with the computer and the computer program, the software, scans the body surface 3 and the measuring zones M(1 . . . n) to have an initial thermographic image of the surface.

Also an initial traditional image is photographed by the camera. The initial traditional image, and the initial thermographic image of the initial surface temperature are recorded and stored in the computer memory device 24.

These images are superimposed on each other in the reporting program in the computer, and are used for illustrating the recovery process. The initial traditional image is particularly important as evidence of the initial state of the body surface and to avoid error sources.

The computer with the software calculates an initial average surface temperature referred to as T: initial M(1 . . . n) for each measuring zone M. The average surface temperature is based on the thermographic image of the body surface showing the temperature in a large number of pixels within each measuring zone.

The computer with the software also calculates an initial average temperature referred to as T: initial for the total body surface comprising all measuring zones M (1–n).

The computer with the software also calculates a zone reference temperature referred to as T: zonref (1–n) for each measuring zones M (1–n) as an average value of the surface temperature of the pixels in each measuring zones M (1–n) measured by thermographic camera.

Thereafter is the difference between the initial average temperature T: initial and the zone reference temperature T zoneref M(1–n) calculated for each measuring zone, the difference is referred to as T: initialdiff M(1–n).

$$T\text{:initialdiff } M(1-n) = T\text{:inital} - T \text{ zoneref } M(1-n)$$

The traditional initial image and the thermographic initial image, the coordinates of the measuring zones, the initial average temperature T: initial, zone reference temperature T: zoneref M(1–n), and the calculated difference T: initialdiff M(1–n) and measuring comments are recorded and stored in the memory device in a computer file with a unique name linked to the person and date.

Exposure Period

During the exposure period is the part of the body exposed to a refrigerant during a predetermined exposure time. Immediately after the exposure time is finalized the time is started to be recorded.

The body part is exposed, cooled, with a refrigerant, in verifiable conditions for 30 seconds, 1 minute or 5 minutes. Cooling of the hands and feet occurs in any of the following harmless ways:

a) Water temperature +5 to +20° C., preferably 12-15° C., the hands are lowered down to the wrists under water for 30 seconds, feet are lowered so that the ankle bump go under water for 45 seconds (more surface cooling). Before dipping the hands into the water, plastic gloves can be placed on the hands they will removed of immediately after cooling. The hands can also be dipped in the water without plastic gloves and wiped (without rubbing) with a towel immediately after cooling. It is preferable to avoid the heating effect that can be cause by drying with a towel. Feet are lowered without protection into the water.

b) Cold rise bath (round grained rice) with a temperature of +5 to +20° C., preferably 12-15° C., hands or feet are immersed in the same manner as above.

c) snow (dry snow) hands or feet are immersed in the same manner as above.

If the face, ears, neck, throat should be examined, these are cooled by preferably a walk, in an ambiance temperature of −5° C. for 10-20 min minutes, for example, in a cold temperature environment with a cold factor of −5° C.

A recovery period begins immediately after ending the exposure time, ie. immediately after the body part is removed from the refrigerant. In this example the recovery means that the tested body part naturally regains heat and returns to the original surface temperature of the body surface.

The body parts are repositioned in front and within the surface area of the background screen 6' in the same position as at the previous initial examination and photographing.

The computer program have means for locating and programming the scanning position, the measuring zone coordinates, for the body part to ensure that the same scanning position for the body part is located and scanned over the entire examination period, both at the initial period and during the recovery period when digital photographing and filming with thermographic camera are carried out.

A traditional image and/or a traditional film of the body surface is photographed or filmed with the thermographic camera.

The traditional image is photographed to determine if a change in temperature is due to residual water on the skin. The resulting images or film provides a controlling tool for the thermographic camera measurements. A traditional still photography shall initially be made with a maximum one-minute intervals.

During the recovery period, ie from the recovery period begins immediately after exposure period has ended, the instants of time for the measurements (photographing and/or filming) progress is recorded. Hereafter the first instant of time is referred to as the starting time t:cold=0, and the finishing instant of time is referred to as tend, which is the instant of time when the measurements ends and the recovery period is finished.

The traditional and thermographic photographing with thermographic camera 4 is repeated with a certain frequency, at least every 30 seconds the first three minutes and then every other minute.

The recovery period is ended when filming with thermographic camera and the on-going software processing of calculations and reporting program show that some, or all of the body surface, all measuring zones M (1–n), have reached a predetermined final temperature T end based on a percentage of the initial average temperature T: initial. The recovery period can also be ended when a predetermined maximum recovery period has passed, where the recovery period is measured from the first photographing or filming with thermographic camera after the exposure period, for example 15 minutes.

The instant of time for each measurement, each traditional or thermographic image, is referred to as t:image and is measured from the starting time t:cold. Also t:image is recorded and saved in the memory device.

The measurement program in the computer is started when the recovery period begins. The body surface is photographed by the thermographic camera and the surface temperature is thereby measured. The resulting thermographic image shows the temperature of body surface.

The body surface is photographed, ie the surface temperature is measured, in the measuring zones M (1–n) at least every two minutes, preferably every minute, preferably every 15 seconds or even every two seconds or every second. The thermographic images are recorded and stored in the memory device.

At the first photographing, directly after cooling, the computer with the software calculates an cold average surface temperature of the entire body surface, hereafter referred to as T: cold. In addition, a cold average surface temperature referred to as T: zonecold M(1–n) for each measuring zone M is calculated.

The cold average surface temperatures are based on the thermographic image of the body surface showing the temperature in a large number of pixels within each measuring zone.

The cold average surface temperature T: cold and the cold average surface temperature T: zonecold M(1–n) are recorded and stored in the memory device 24.

When filming with the thermographic camera, the recovery process is recorded and documented and exact instants of time for each image, hereafter referred to as tp:M(1–n) are measured from the time t:cold.

At each instant of photographing and measuring, a recovery temperature hereafter referred to as T: zonerecover M(1–n) is calculated for each measuring zones M (1–n). The recovery temperature is calculated as an average value of the surface temperature of all picture points, pixels, in each measuring zones M (1–n) measured by the thermo graphic camera.

The instants of time of the images, tp:M(1–n) and the recovery temperature T: zonerecover M(1–n) are recorded and stored in the memory device 24.

Thereafter are the following differences are calculated:

$$T{:}zonerecover\ M(1\text{-}n) - T{:}cold\ M(1\text{-}n) = T{:}recoverdiff\ (1\text{-}n)(temperature) \qquad 1)$$

$$t{:}cold - t{:}end = t{:}recoverdiff(time) \qquad 2)$$

$$T\ zonerecover\ M(1\text{-}n) - T{:}zoneref\ M(1\text{-}n) = T{:}zonediff\ M(1\text{-}n)(temperature) \qquad 3)$$

$$tp(1\text{-}n) - t{:}cold = t{:}zonediff(time) \qquad 4)$$

The calculated differences T: recoverdiff M(1–n), t: recoverdiff, T: zonediff M(1–n) and t: zondiff are recorded and stored in the memory device into one vector per measuring zones M (1–n) connected to the individual-specific data file.

All thermographic film footage, traditional and thermographic photos, measuring zones coordinates, the average temperature T: cold, the recovery temperature T: zonerecover M(1–n), the time tp (1–n), t: cool, t: end, t: image, in all measuring zones at all measurement occasions, and the calculated differences T recoverdiff M(1–n), t: recoverdiff in all measuring zones at all measurement occasions, and measurments comments are recorded and stored in the memory device into a computer file with unique name associated with the individual and date.

Audio recording of comments during the recovery period can also be recorded and saved. New measuring comments are possible to insert, after which the collected data to can be inserted to an already previously created file. The recovery process is displayed in graphs on the screen and the recovery period as numerical values per zone.

Analysis of Results

For the simultaneous examination of the left and right body part, the differences T: initialdiff, T: recoverdiff M(1–n), T: zonediff M(1–n), t: recoverdiff and t: zondiff for the different body parts are calculated and stored in the memory device. Surface temperature deviations between left and right body and corresponding measuring zones, are calculated, recorded, compared and stored in the memory device. This comparison indicates if there are measuring zones with reduced blood circulation. The differences are individual, and only indicates variation between the left and the right corresponding body surfaces of a single person.

The subsequent analysis will determine the measuring zones where strong cooling effect is obtained or where the recovery process is slow. The recovery process can be observed and compared in each measuring zone can be compared with the total body surface of the examined body part, and also between adjacent measuring zones.

The recovery process can take several forms, such as linear or non linear. The collected information in the memory device such as saved temperature data and time data are processed and introduced into the reporting program for visualization in graphs and profiles like an individual profile curve on a graph.

Temperature data is converted to the profile data and plotted in a figure which illustrates the recovery process.

The areas indicated by the responses of the questionnaire recurs in the analysis automatically as possible problem areas.

The measuring zones corresponding to areas of the body part where the blood circulation has been affected by the cold-provocation can be further examined. Areas which appear to be sensitive and recovery time can be recorded and documented. The presented results only represent an intermediate result, and because there are individual differences between people, further studies need to be carried out to validate and confirm if there are any problems with the blood circulation in the indicated areas, measuring zones.

In the embodiment described above, a number of different operations and calculations are executed by the computer program on the computer in order to have results from the examination. Additional operations that the computer program performs when it is executed on the computer and reporting to the reporting program during the measurement period are for example the following:

With reference to Table 1 below the computer iterates the following program steps:

Initial Period

The difference between the surface temperature T: inital and the zone's average temperature T: zoneref M(1–n) is calculated during the initial period, registered and grouped in intervals of measuring zones with 0.01 degree difference, measuring zones with 0.1 degree difference, etc. Each measuring zones M (1–n) can be identified and correlated with the responses.

Directly after Cooling and During the Recovery Period

The difference between the total surface average temperature T: cold and the measuring zones average temperature T: zonecold M(1–n) are calculated and recorded and grouped in intervals of zones with 0.01 degree difference, zones with 0.1 degree difference, etc. Each measuring zones M(1–n) can be identified and correlated with the answers from the questionnaire. Comparison is also done with results from the initial period.

After Recovery

The differences between the surface temperature T: end, and the measuring zones average recovery temperature T: zonerecover M(1–n) are calculated continuously during the recovery period and recorded and grouped in intervals of zones with 0.01 degree difference, zone with 0.1 degree difference, etc. Each measuring zones M (1–n) can be identified and correlated with the responses. Comparison is also done with results from the initial period and immediately after cooling. Time for recovery per zone is also calculated.

TABLE 1

| Values | Measurments Initial | Measurments Directly after cooling | Measurments after recovery | Time for recovery |
|---|---|---|---|---|
| Measuring zone temperature | T:zoneref M(1 − n) | T:zonecold M(1 − n) | T:zonerecover M(1 − n) | tp M(1 − n) |
| The average temperature of the whole surface | T:initial | T:cold | T:end | t:diff = t:end − t:cold |
| Differences average temperature versus measuring zone temperature | T:initialdiff M(1 − n) = T:inital − T:zoneref M(1 − n) | T:cold M(1 − n) − T:zonecold M(1 − n) | T:diff M(1 − n) = T:end − T:zonerecover M(1 − n) | t:diff = t:end − t:cold |

T = temperature,
t = time

Figure 7:
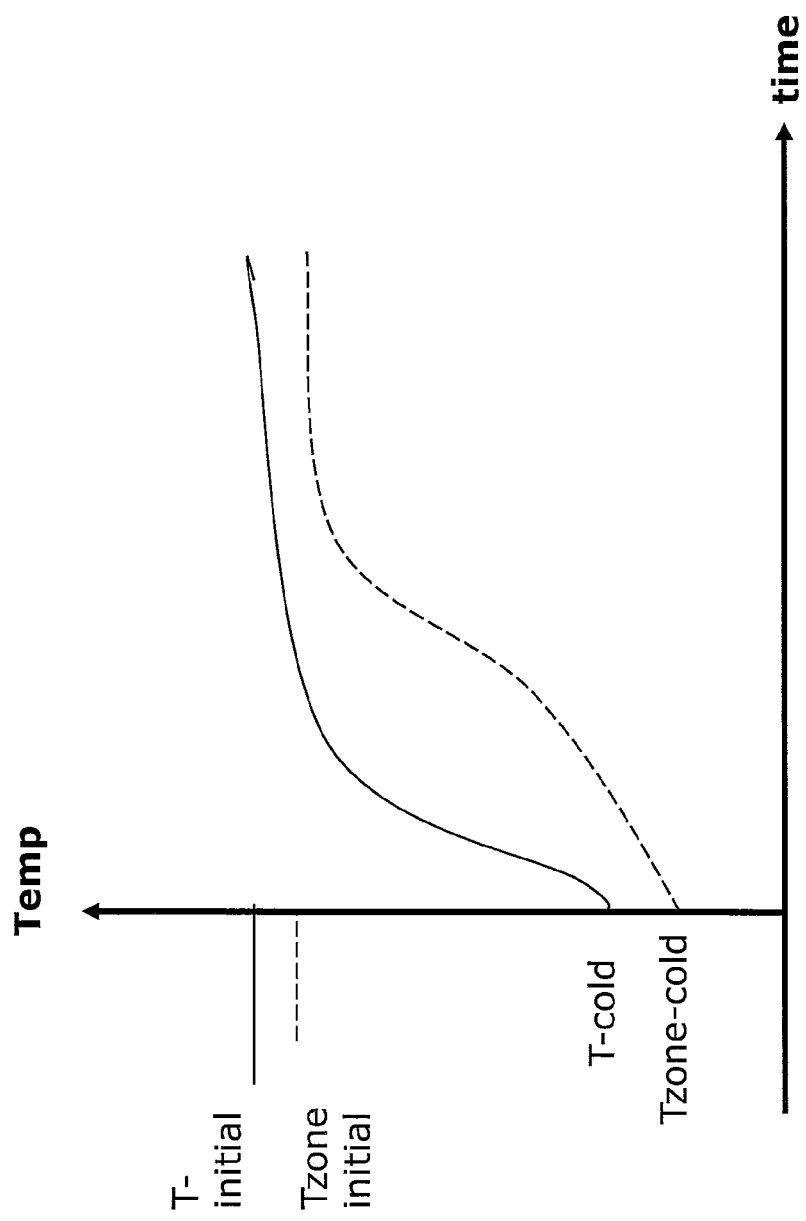
FIG. 7 shows a graph of the recovery process for a body part examined with the method according to the invention.

The time for recovery of the cooled body part to regain the reference temperature is recorded, and if it is straight-line or according to other processes, see FIG. 7. This figure shows a recovery process for an individual measuring zone Tzone and recovery process for the entire surface Tsurface. The curve for Tzone indicates that the body part has been more affected by the cold-provocation that the rest of the examined body surface. This is an indication that the particular measuring zone should be further examined to verify if the body part has an injury in this measuring zone, for example a freezing injury, which affects the blood circulation.

The present invention should not be limited to the description above and the drawings but can be changed and modified in a variety of ways within the framework of the subsequent patent claims.

The invention claimed is:

1. A method for examination of a surface temperature of a first body part and a second body part of a subject of examination, each body part comprising a body surface, and each body surface comprising a number of measuring zones for examination, the method comprising:
   during an initial period, positioning each body part in a system for examining said each body part, wherein the system comprises a thermographic camera and a background screen, the thermographic camera configured to digitally photograph each body part as both a traditional image and a thermographic image, the traditional image being a monochrome or color photograph of the body surface of each body part,
   during the initial period, for each body part, acquiring a first traditional image of the body surface of each body part and acquiring a first thermographic image of the body surface of each body part with the thermographic camera,
   during an exposure period that follows the initial period, exposing each body part to a refrigerant for a predetermined exposure time,
   during a recovery period that follows the exposure period, repositioning each body part in the system,
   during the recovery period, acquiring a second traditional image of each body part with the thermographic camera and filming the body surface of each body part as a thermographic film or repetitively acquiring thermographic images of the body surface of each body part,
   wherein the positioning and the repositioning each body part in the system comprises positioning each body part on an opposite side of the background screen from the rest of the subject so as to reduce an effect of heat from the rest of the subject on the examination of the surface temperature of each body part while filming or acquiring the images, the background screen including a cutout through which each body part is inserted to face the thermographic camera, wherein the background screen is kept at a temperature that is different from the surface temperature of each body part by at least two degrees,
   analyzing, with a computer, a recovery process of the surface temperature in the measuring zone of the body surface of each body part, wherein the recovery process is based on the surface temperature within each measuring zone measured by the thermographic camera during the initial period and the recovery period,
   evaluating, with the computer, the recovery process of the surface temperature in each measuring zone based on at least one of: deviations of temperature data between the first and second body parts, or deviations of temperature data between individual measuring zones and the whole body surface which includes all the measuring zones, and
   displaying, with the computer, results of the evaluating the recovery process.

2. The method according to claim 1, wherein the method further comprising:
   storing the images and the films in a memory device,
   recording and storing the acquisition time for each image and/or film,
   the analyzing and evaluating further comprises calculating a zone reference temperature for each measuring zone, calculating an initial average temperature for all measuring zones, repetitively calculating a recovery temperature for each measuring zone, wherein the recovery temperature is based on the surface temperature within each measuring zone calculating a difference between the recovery temperature and the zone reference temperature for each measuring zone and recording and storing the calculated difference in the memory device,
   recording and storing the recovery temperature for each measuring zone and the acquisition time of the respective image in the memory device,
   ending the recovery period when all measuring zones have reached a predetermined final temperature based on an initial average temperature, or when a predetermined maximum recovery period has passed, recording and storing in the memory device a duration for each measuring zone to reach the predetermined final temperature.

3. The method according to claim 1, wherein each body part is selected from the group consisting of: hands, feet, arms, legs, features of the face of the subject, the neck and a back of the neck of the subject, ears, and cheeks.

4. The method according to claim 2, wherein the calculating the zone reference temperature and repetitively calculating the recovery temperature is based on average surface temperature variations in a measuring zone.

5. The method according to claim 2, further comprising: calculating differences in the initial average temperature, the zone reference temperature, the recovery temperature and the recovery period between the first and the second body part and the respective corresponding measuring zones, further comprising comparing and storing the calculated differences in the memory device.

6. The method according to claim 2, wherein the displaying results comprises an individual profile curve on a graph based on the temperature data and acquisition times stored in the memory device.

7. The method according to claim 2, wherein the traditional and thermographic images are acquired at least every two minutes during the recovery period.

8. A computer program that is loaded into an internal memory of a computer, comprising the code parts of the computer program product for carrying out the method steps recited in claim 2 when it is executed on the computer.

9. A memory medium comprising a computer program according to claim 8.

10. A non-transitory computer-readable storage medium having computer-executable instructions, the computer-executable instructions comprising instructions for performing the method steps recited in claim 2.

* * * * *